(12) United States Patent
Tsunamoto

(10) Patent No.: US 10,235,968 B2
(45) Date of Patent: Mar. 19, 2019

(54) MEDICAL IMAGE DISPLAY APPARATUS, MEDICAL IMAGE ADJUSTMENT METHOD AND RECORDING MEDIUM

(71) Applicant: KONICA MINOLTA, INC., Chiyoda-ku, Tokyo (JP)

(72) Inventor: Yuki Tsunamoto, Tachikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 109 days.

(21) Appl. No.: 15/412,687

(22) Filed: Jan. 23, 2017

(65) Prior Publication Data
US 2017/0213524 A1 Jul. 27, 2017

(30) Foreign Application Priority Data
Jan. 25, 2016 (JP) .................................. 2016-011194

(51) Int. Cl.
*G09G 5/10* (2006.01)
*G06F 19/00* (2018.01)
(Continued)

(52) U.S. Cl.
CPC ............... *G09G 5/10* (2013.01); *G06F 19/00* (2013.01); *G06F 19/321* (2013.01); *G09G 5/00* (2013.01); *G16H 40/63* (2018.01); *G06T 7/0012* (2013.01); *G09G 2320/0238* (2013.01); *G09G 2320/0626* (2013.01); *G09G 2320/0633* (2013.01); *G09G 2320/0646* (2013.01); *G09G 2380/08* (2013.01)

(58) Field of Classification Search
CPC .... G09G 5/10; G09G 5/00; G09G 2320/0238; G09G 2320/0626; G09G 2320/0633; G09G 2320/0646; G09G 2380/08; G16H 40/63; G06F 19/00; G06F 19/321; G06T 7/0012
See application file for complete search history.

(56) References Cited

U.S. PATENT DOCUMENTS 7,298,383 B2 * 11/2007 Vuylsteke ............... G06T 5/009
345/426
2003/0123719 A1 * 7/2003 Kurahashi ............. G06F 19/321
382/131
(Continued)

FOREIGN PATENT DOCUMENTS

JP 2015070999 A 4/2015

*Primary Examiner* — Yu Chen
(74) *Attorney, Agent, or Firm* — Holtz, Holtz & Volek PC

(57) ABSTRACT

A medical image display apparatus, including: a storage section; a display section; a specification section which receives user's specification of medical image data as an adjustment reference; a display control section which controls the display section to display an adjustment reference medical image on the basis of the medical image data as the adjustment reference and a density adjustment value associated with the medical image data; an adjustment instruction section which receives user's instruction to perform density adjustment of the adjustment reference medical image displayed on the display section; and an overall adjustment section which, for each piece of medical image data other than the medical image data as the adjustment reference, changes a density adjustment value associated with the medical image data on the basis of change information indicating a content changed by the density adjustment.

5 Claims, 7 Drawing Sheets

(51) Int. Cl.
    *G09G 5/00*           (2006.01)
    *G16H 40/63*        (2018.01)
    *G06T 7/00*           (2017.01)

(56) References Cited

U.S. PATENT DOCUMENTS

| | | | | |
|---|---|---|---|---|
| 2004/0151358 A1* | 8/2004 | Yanagita | ............... | G06F 19/321 |
| | | | | 382/132 |
| 2004/0252132 A1* | 12/2004 | Vuylsteke | ............... | G06T 5/009 |
| | | | | 345/617 |
| 2009/0048874 A1* | 2/2009 | Sasano | .................. | G06F 19/321 |
| | | | | 705/3 |
| 2009/0175417 A1* | 7/2009 | Sasano | .................... | G06F 19/321 |
| | | | | 378/98.5 |
| 2010/0128063 A1* | 5/2010 | Huo | ...................... | G06F 19/321 |
| | | | | 345/620 |
| 2010/0171682 A1* | 7/2010 | Chen | .................... | G06F 19/321 |
| | | | | 345/55 |
| 2013/0111353 A1* | 5/2013 | Ueda | ...................... | G06Q 10/10 |
| | | | | 715/748 |
| 2013/0198687 A1* | 8/2013 | Bird | ...................... | A61B 5/7425 |
| | | | | 715/810 |
| 2013/0343622 A1* | 12/2013 | Ruiz | .................... | G06T 11/008 |
| | | | | 382/131 |
| 2014/0177803 A1* | 6/2014 | Stevens | ................... | A61B 6/52 |
| | | | | 378/98 |
| 2015/0363053 A1* | 12/2015 | Aoyama | ............... | G06F 3/0482 |
| | | | | 715/838 |
| 2016/0253455 A1* | 9/2016 | Hasegawa | ............. | G06F 19/321 |
| | | | | 705/2 |

* cited by examiner

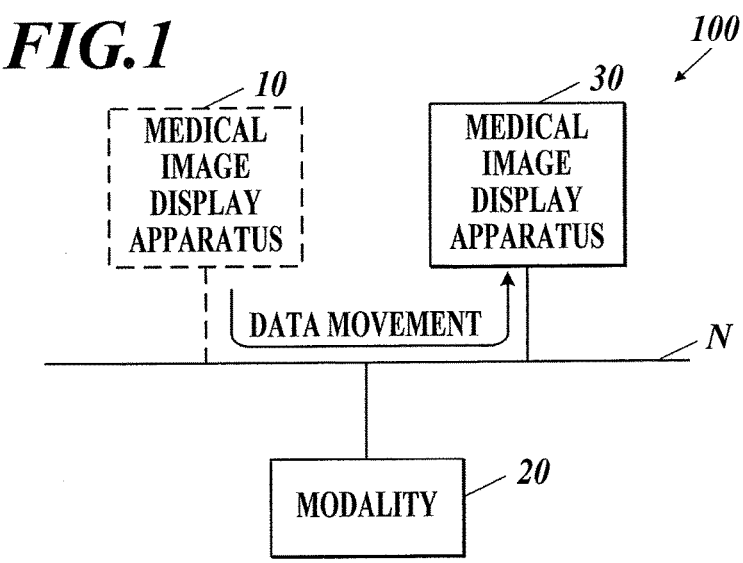
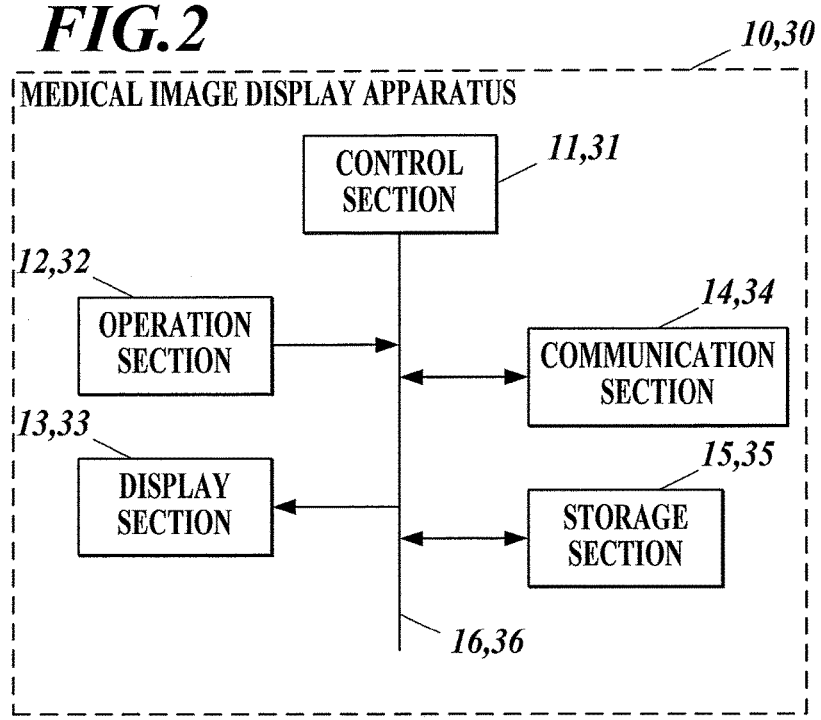

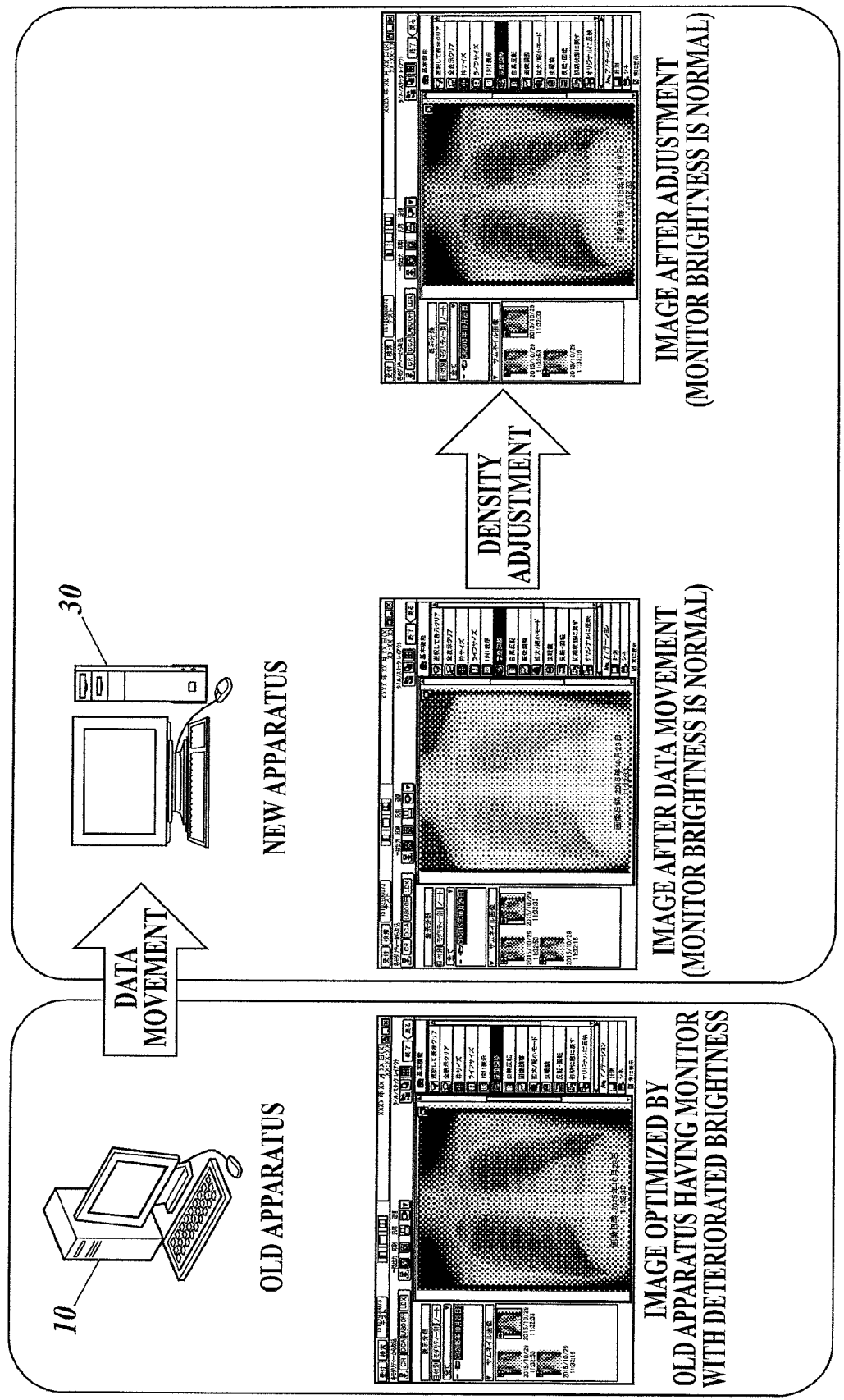

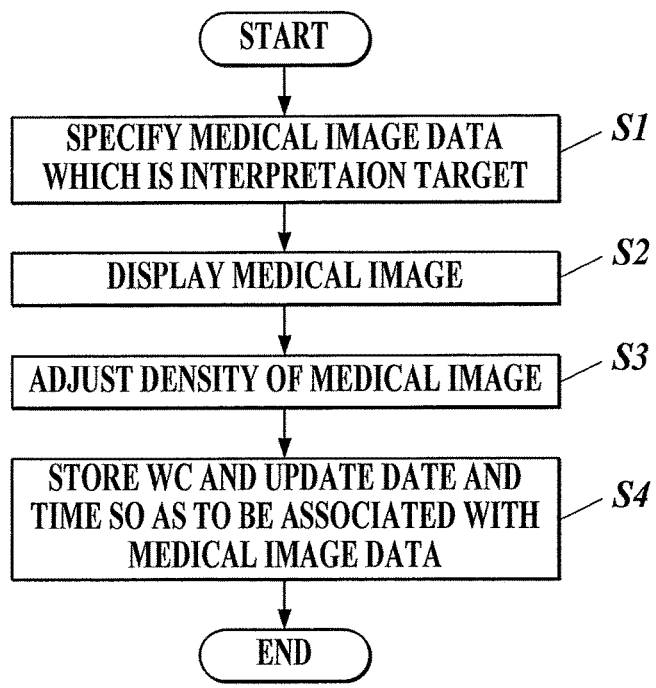

MEDICAL IMAGE DISPLAY APPARATUS, MEDICAL IMAGE ADJUSTMENT METHOD AND RECORDING MEDIUM

BACKGROUND OF THE INVENTION

1. Field of the Invention

The present invention relates to a medical image display apparatus, a medical image adjustment method and a recording medium.

2. Description of Related Art

In the medical field, diagnosis by image interpretation is performed by displaying medical images, which were generated by various modalities (image generation apparatuses), and observing the states of lesions by doctors. With the spread of medical image management systems such as PACS (Picture Archiving and Communication System), medical images generated by modalities such as CR (Computed Radiography), CT (Computed Tomography) and MRI (Magnetic Resonance Imaging) are stored as digital images.

In the medical image interpretation, density adjustment is performed according to doctors' operations in order to display images appropriate for the diagnosis by, for example, changing densities so that the doctors can easily find the lesions in the displayed images. Information regarding the adjusted densities (density adjustment values) is stored so as to be associated with the respective medical images. Thus, when the medical images are displayed again later, the images are displayed in optimized states on the basis of the density adjustment values.

For example, as a technique for performing tone correction of medical images, there is suggested a medical image display apparatus which can display medical images with appropriate tones without performing modification corresponding to tone correction to individual applications having functions of displaying medical images even when the hardware is not provided with functions for performing color management (see Japanese Patent Application Laid Open Publication No. 2015-70999, hereinafter referred to as Patent document 1). The medical image display apparatus uses a look-up table for GSDF (Grayscale Standard Display Function) conversion which was created in advance.

However, the brightness of monitor displaying medical images is deteriorated according to the use. Thus, there has been a problem that, when medical images are displayed on new monitors after replacement of PACS including old monitors (data movement) in medical facilities, the medical images are excessively bright when the images are displayed by using the density adjustment values which were stored when the images were displayed on the old monitors before the replacement.

Furthermore, the technique described in Patent document 1 requires measuring the display tone characteristic information of display apparatus by a calibration tool (for example, Medical QA web Mobile made by Barco corporation) and creating a look-up table for GSDF conversion. Thus, the work for tone adjustment has been troublesome.

SUMMARY OF THE INVENTION

The present invention has been made in consideration of the above problems in the conventional techniques, and an object of the present invention is to easily perform density adjustment to have optimized densities without using special tools for medical image data having densities adjusted in other medical image display apparatuses.

In order to achieve the above object, according to one aspect of the present invention, there is provided a medical image display apparatus, including: a storage section which stores a plurality of pieces of medical image data, each of the plurality of pieces of medical image data being moved from another medical image display apparatus and associated with a density adjustment value regarding a density which is adjusted when a medical image is displayed on the basis of the medical image data in the another medical image display apparatus; a display section which displays a medical image on the basis of medical image data stored in the storage section; a specification section which receives user's specification of medical image data as an adjustment reference among the plurality of pieces of medical image data stored in the storage section; a display control section which controls the display section to display an adjustment reference medical image on the basis of the medical image data as the adjustment reference and a density adjustment value associated with the medical image data; an adjustment instruction section which receives user's instruction to perform density adjustment of the adjustment reference medical image displayed on the display section; and an overall adjustment section which, for each piece of medical image data other than the medical image data as the adjustment reference among the plurality of pieces of medical image data stored in the storage section, changes a density adjustment value associated with the medical image data on the basis of change information indicating a content changed by the density adjustment performed to the adjustment reference medical image.

Preferably, in the medical image display apparatus, the change information is a change value indicating a difference between density adjustment values before and after the density adjustment, the density adjustment values being associated with the medical image data as the adjustment reference.

Preferably, in the medical image display apparatus, a single piece of medical image data is the adjustment reference, and for each piece of the medical image data other than the medical image data as the adjustment reference, the overall adjustment section adds the change value to the density adjustment value associated with the medical image data.

Preferably, in the medical image display apparatus, a plurality of pieces of medical image data is the adjustment reference, the medical image display apparatus further includes a table creating section which, for each of the plurality of pieces of medical image data as the adjustment reference, creates a correspondence table associating update date and time with the change value of the medical image data, the update date and time being latest date and time when the density adjustment value associated with the medical image data is updated in the another medical image display apparatus, and for each piece of the medical image data other than the medical image data as the adjustment reference, the overall adjustment section calculates a change value corresponding to the update date and time of the medical image data on the basis of the correspondence table and adds the calculated change value to the density adjustment value associated with the medical image data.

Preferably, in the medical image display apparatus, the specification section is capable of receiving specification of the medical image data as the adjustment reference by a predetermined classification of the plurality of pieces of medical image data stored in the storage section, and for each piece of the medical image data other than the medical image data as the adjustment reference among the plurality of pieces of medical image data stored in the storage section, the overall adjustment section changes the density adjustment value associated with the medical image data on the basis of the change information which is obtained by the predetermined classification.

Preferably, in the medical image display apparatus, the predetermined classification is a modality type, an apparatus type, an image size, a site, a patient or a combination thereof.

According to another aspect of the present invention, there is provided a medical image adjustment method for a medical image display apparatus that includes: a storage section which stores a plurality of pieces of medical image data, each of the plurality of pieces of medical image data being moved from another medical image display apparatus and associated with a density adjustment value regarding a density which is adjusted when a medical image is displayed on the basis of the medical image data in the another medical image display apparatus; and a display section which displays a medical image on the basis of medical image data stored in the storage section, the method including: receiving user's specification of medical image data as an adjustment reference among the plurality of pieces of medical image data stored in the storage section; controlling the display section to display an adjustment reference medical image on the basis of the medical image data as the adjustment reference and a density adjustment value associated with the medical image data; receiving user's instruction to perform density adjustment of the adjustment reference medical image displayed on the display section; and for each piece of medical image data other than the medical image data as the adjustment reference among the plurality of pieces of medical image data stored in the storage section, changing a density adjustment value associated with the medical image data on the basis of change information indicating a content changed by the density adjustment performed to the adjustment reference medical image.

According to another aspect of the present invention, there is provided a non-transitory computer readable recording medium storing a program for a computer of a medical image display apparatus that includes: a storage section which stores a plurality of pieces of medical image data, each of the plurality of pieces of medical image data being moved from another medical image display apparatus and associated with a density adjustment value regarding a density which is adjusted when a medical image is displayed on the basis of the medical image data in the another medical image display apparatus; and a display section which displays a medical image on the basis of medical image data stored in the storage section, the program causing the computer to function as: a specification section which receives user's specification of medical image data as an adjustment reference among the plurality of pieces of medical image data stored in the storage section; a display control section which controls the display section to display an adjustment reference medical image on the basis of the medical image data as the adjustment reference and a density adjustment value associated with the medical image data; an adjustment instruction section which receives user's instruction to perform density adjustment of the adjustment reference medical image displayed on the display section; and an overall adjustment section which, for each piece of medical image data other than the medical image data as the adjustment reference among the plurality of pieces of medical image data stored in the storage section, changes a density adjustment value associated with the medical image data on the basis of change information indicating a content changed by the density adjustment performed to the adjustment reference medical image.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 1 is a system configuration view of a medical image management system;

FIG. 2 is a block diagram showing a functional configuration of medical image display apparatuses;

FIG. 3 is a view showing an outline of the present invention;

FIG. 4 is a flowchart showing medical image display processing executed in the medical image display apparatus before data movement;

DETAILED DESCRIPTION OF THE PREFERRED EMBODIMENT

Figure 5:
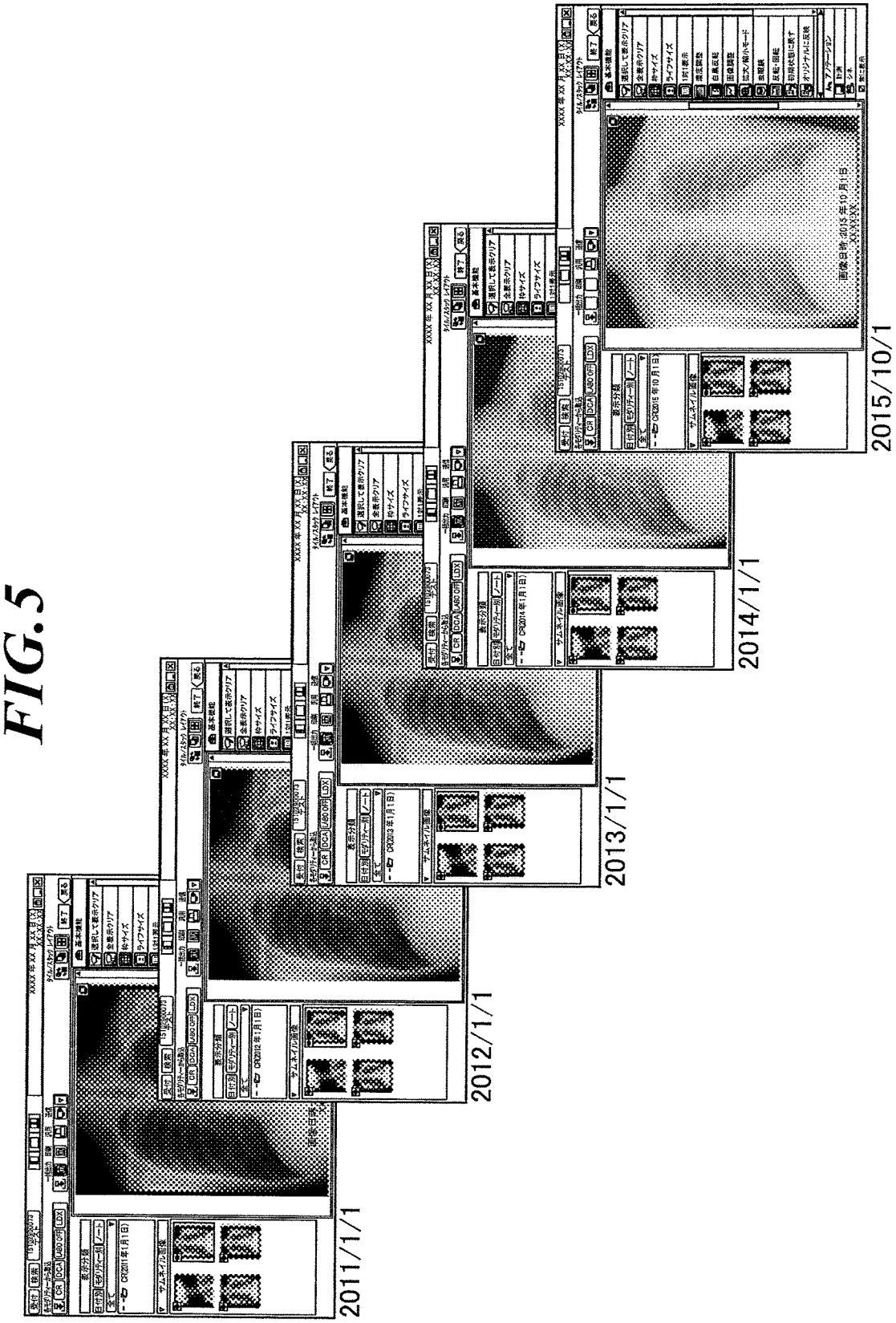
FIG. 5 is display examples of a case where medical image data having a density optimized in an old medical image display apparatus is moved to a new medical image display apparatus and the medical image is displayed before performing density adjustment.

Hereinafter, an embodiment of the present invention will be described. The present invention is not limited to the illustrated examples.

FIG. 1 shows a system configuration of a medical image management system 100. As shown in FIG. 1, the medical image management system 100 is configured by connecting a medical image display apparatus 10 with a modality 20 so as to communicate data via a communication network N such as a LAN (Local Area Network). The DICOM (Digital Imaging and Communication in Medicine) standard is applied to the communication network N.

The medical image display apparatus 10 stores image data (medical image data) of medical images generated by various modalities 20. The medical image display apparatus 10 is also used when a medical image is displayed on the basis of medical image data and a user that is a doctor interprets the medical image.

The medical image data is a DICOM file generated in a format which meets the DICOM standard. The medical image data is formed of an actual image data part and a header. The header contains accompanying information (patient information, test information, series information and such like) regarding the medical image. The patient information includes information such as a patient ID, a patient name, sex and birth date for identifying the patient. The test information includes information such as a test ID, test date and time and test conditions for identifying the test. The series information includes information such as a series number and a tested site for identifying the series in a same test.

FIG. 2 shows a functional configuration of the medical image display apparatus 10. As shown in FIG. 2, the medical image display apparatus 10 is configured by including a control section 11, an operation section 12, a display section 13, a communication section 14, a storage section 15 and such like, and the sections are connected to each other via a bus 16.

The control section 11 is configured by including a CPU (Central Processing Unit) and such like, and integrally controls processing operations of the sections in the medical image display apparatus 10. Specifically, the control section 11 reads out various processing programs stored in the storage section 15 and performs various types of processing in cooperation with the programs.

The operation section 12 is configured by including a keyboard including character input keys, numeric keys and various types of function keys and a pointing device such as a mouse. The operation section 12 outputs an operation signal which was input by user's key operation to the keyboard or mouse operation to the pointing device to the control section 11.

The display section 13 is configured by including an LCD (Liquid Crystal Display) and displays various screens in accordance with display data which was input from the control section 11. The display section 13 displays a medical image and such like. The brightness of display section 13 is deteriorated according to the use and gradually lowered.

The communication section 14 is an interface which performs transmission and reception of data with external equipment such as the modality 20.

The storage section 15 is configured by including a hard disk, a nonvolatile semiconductor memory or the like and stores various types of data. Specifically, the storage section 15 stores a plurality of pieces of medical image data, various processing programs and such like.

In a case where the medical image display apparatus 10 is used in the medical image management system 100, when a user interprets a medical image, the control section 11 controls the display section 13 to display the medical image on the basis of medical image data stored in the storage section 15 and a density adjustment value associated with the medical image data.

The user adjusts the density of the medical image by an operation to the operation section 12 while watching the medical image displayed on the display section 13. Here, any value such as brightness and luminance may be used as the density as long as the value is an index indicating the density of image. The control section 11 stores a density adjustment value regarding the adjusted density (tone) and update date and time so as to be associated with the medical image data, the update date and time being the latest date and time when the density adjustment value was updated. The density adjustment value includes a window center (WC) and a window width (WW), for example. In the embodiment, the WC is used as the density adjustment value. Specifically, the control section 11 associates the WC obtained by density adjustment of the medical image and the update date and time (density adjustment date and time) with the medical image data by writing the WC and the update date and time into the header of the medical image data.

Here, window level conversion processing (tone conversion) will be described. The window level conversion processing is processing for converting a pixel value (signal value) of each of the pixels, which form the image stored in the image file, into a tone (gray level) which can be expressed on the monitor (display section 13). The correspondence relation of an output value (gray level) of the monitor to the pixel value, that is, the correspondence relation between input and output values in the window level conversion processing is determined by the two parameters of WC and WW. The WC is a center value of the target region of the window level conversion processing. The WW is a width of the target region of the window level conversion processing. In the window level conversion processing, pixel values in the range included in the width WW and having the WC as the center are converted into density values of 0 to 255. When the WC is changed, the brightness of image is changed. When the WW is changed, the contrast of image is changed. In the embodiment, only the WC is changed by density adjustment, and the WW is fixed (that is, not changed by the density adjustment) for each piece of medical image data.

The control section 11 moves a plurality of pieces of medical image data stored in the storage section 15 from the medical image display apparatus 10 to a new medical image display apparatus 30. Specifically, the control section 11 transmits the plurality of pieces of medical image data stored in the storage section 15 to the medical image display apparatus 30 via the communication section 14.

The modality 20 photographs the diagnosis target site of the patient and performs digital conversion to the obtained image to generate medical image data. The modality 20 is, for example, configured by including a CR, CT or MRI. The modality 20 attaches the accompanying information to the medical image data by writing the accompanying information into the header of the medical image data on the basis of the DICOM standard.

The following description is made by taking, as an example, a case where the new medical image display apparatus 30 is introduced to replace the old medical image display apparatus 10 in the above-described medical image management system 100. At data movement from the medical image display apparatus 10 to the medical image display apparatus 30, the medical image display apparatus 30 is also connected to the communication network N, and the medical image display apparatus 10 and the medical image display apparatus 30 are connected to each other so as to perform data communication.

As shown in FIG. 2, the medical image display apparatus 30 is configured by including a control section 31, an operation section 32, a display section 33, a communication section 34, a storage section 35 and such like, and the sections are connected to each other via a bus 36.

The explanation of the medical image display apparatus 30 is omitted for the same configurations as those of the medical image display apparatus 10, and only the configuration characteristic of the medical image display apparatus 30 will be described.

At data movement from the medical image display apparatus 10 to the medical image display apparatus 30, a plurality of pieces of medical image data stored in the storage section 15 of the medical image display apparatus 10 is transmitted to the medical image display apparatus 30 and stored in the storage section 35 of the medical image display apparatus 30.

When the data movement is finished, only the medical image display apparatus 30 among the medical image display apparatus 10 and the medical image display apparatus 30 is connected to the communication network N, and the medical image display apparatus 10 is disconnected from the communication network N.

The plurality of pieces of medical image data stored in the storage section 35 was moved from the other medical image display apparatus 10. Each piece of medical image data is associated with a density adjustment value (WC) regarding a density which was adjusted when a medical image was displayed in the other medical image display apparatus 10 on the basis of the medical image data.

The operation section 32 is used when the user specifies medical image data as an adjustment reference among the plurality of pieces of medical image data stored in the storage section 35 and when the user instructs density adjustment of the adjustment reference medical image displayed on the display section 33. That is, the operation section 32 functions as a specification section and an adjustment instruction section.

The control section 31 controls the display section 33 to display the adjustment reference medical image on the basis of the medical image data as the adjustment reference and the WC associated with the medical image data. That is, the control section 31 functions as a display control section.

For each piece of medical image data which is other than the medical image data as the adjustment reference among the plurality of pieces of medical image data stored in the storage section 35, the control section 31 changes the WC associated with the medical image data on the basis of change information indicating a content changed by the density adjustment which was performed to the adjustment reference medical image. That is, the control section 31 functions as an overall adjustment section.

In the embodiment, a change value (hereinafter, referred to as a WC change value) is used as the change information, the change value indicating the difference between WCs before and after the adjustment, the WCs being associated with the medical image data as the adjustment reference.

Specifically, in a case where a single piece of medical image data is the adjustment reference, for each piece of medical image data which is other than the medical image data as the adjustment reference, the control section 31 adds the WC change value of the medical image data as the adjustment reference to the WC associated with the medical image data.

In a case where a plurality of pieces of medical image data is the adjustment reference, for each of the plurality of pieces of medical image data as the adjustment reference, the control section 31 creates a correspondence table associating update date and time with the WC change value of the medical image data, the update date and time being the latest date and time when the WC associated with the medical image data was updated in the other medical image display apparatus 10. That is, the control section 31 functions as a table creating section.

For each piece of medical image data which is other than the medical image data as the adjustment reference, on the basis of the correspondence table, the control section 31 calculates the WC change value corresponding to the update date and time of the medical image data by the interpolation method or the extrapolation method and adds the calculated WC change value to the WC associated with the medical image data.

FIG. 3 shows an outline of the present invention. The medical image data having the density optimized in the medical image display apparatus 10 (old apparatus) which has a deteriorated brightness of the monitor (display section 13) is moved to the medical image display apparatus 30 (new apparatus) which has a normal brightness of the monitor (display section 33). In the medical image display apparatus 30, the medical image is displayed on the basis of the medical image data and the WC associated with the medical image data. Since the WC is the value which was optimized in the medical image display apparatus 10, when the medical image is displayed on the display section 33 of the medical image display apparatus 30, the brightness is excessively high (density is excessively low), which is not appropriate for image diagnosis. Thus, the density needs to be changed to a density appropriate for the medical image display apparatus 30 by performing density adjustment. In the present invention, density adjustment is manually performed to a single piece of or a plurality of pieces of medical image data, and on the basis of the adjustment result, the same density adjustment is reflected on the other pieces of medical image data in the medical image display apparatus 30.

Next, the operation will be described.

FIG. 4 is a flow chart showing medical image display processing executed in the medical image display apparatus 10 before data movement. The processing is performed when a user that is a doctor interprets a medical image, and the processing is executed by software processing in cooperation between the control section 11 and the program stored in the storage section 15.

First, when the user specifies medical image data which is an interpretation target from among a plurality of pieces of medical image data stored in the storage section 15 by the operation to the operation section 12 (step S1), the control section 11 reads out the specified medical image data from the storage section 15, and controls the display section 13 to display a medical image on the basis of the read medical image data (step S2). At this time, the control section 11 performs image processing such as window level conversion processing to the specified medical image data by using the WC and WW associated with the medical image data, and outputs the gray level after the image processing to the display section 13.

Next, the control section 11 performs density adjustment of the medical image according to user's operation to the operation section 12 (step S3). For example, rotations in forward and backward directions of a mouse wheel respectively correspond to the operation of increasing the density (darkening) of the image and the operation of decreasing the density (brightening) of image. The user changes the image density by rotating the mouse wheel forward or backward. The WC is changed by the density adjustment of image.

Next, the control section 11 stores the WC obtained by the density adjustment and the update date and time (current date and time), which is the latest date and time when the WC was updated, so as to be associated with the medical image data which is the interpretation target (step S4). Specifically, the control section 11 writes the WC and the update date and time as accompanying information into the header of the medical image data which is the interpretation target.

Then, the medical image display processing ends.

In such way, for each piece of medical image data, the medical image display apparatus 10 associates the WC with the medical image data, the WC being determined by density adjustment when the medical image was interpreted.

FIG. 5 is display examples of a case where medical image data having densities optimized in the medical image display apparatus 10 is moved to the medical image display apparatus 30 and medical images are displayed on the display section 33 before execution of density adjustment in the medical image display apparatus 30. Each piece of medical image data is associated with the WC corresponding to the update date and time (latest date and time when the WC was updated in the medical image display apparatus 10) of the medical image data. Thus, when a medical image is displayed on the basis of the medical image data and WC associated with the medical image data, a newer medical image (update date and time is closer to the present) is brighter and an older medical image (update date and time is farther from the present) is darker.

Figure 6:
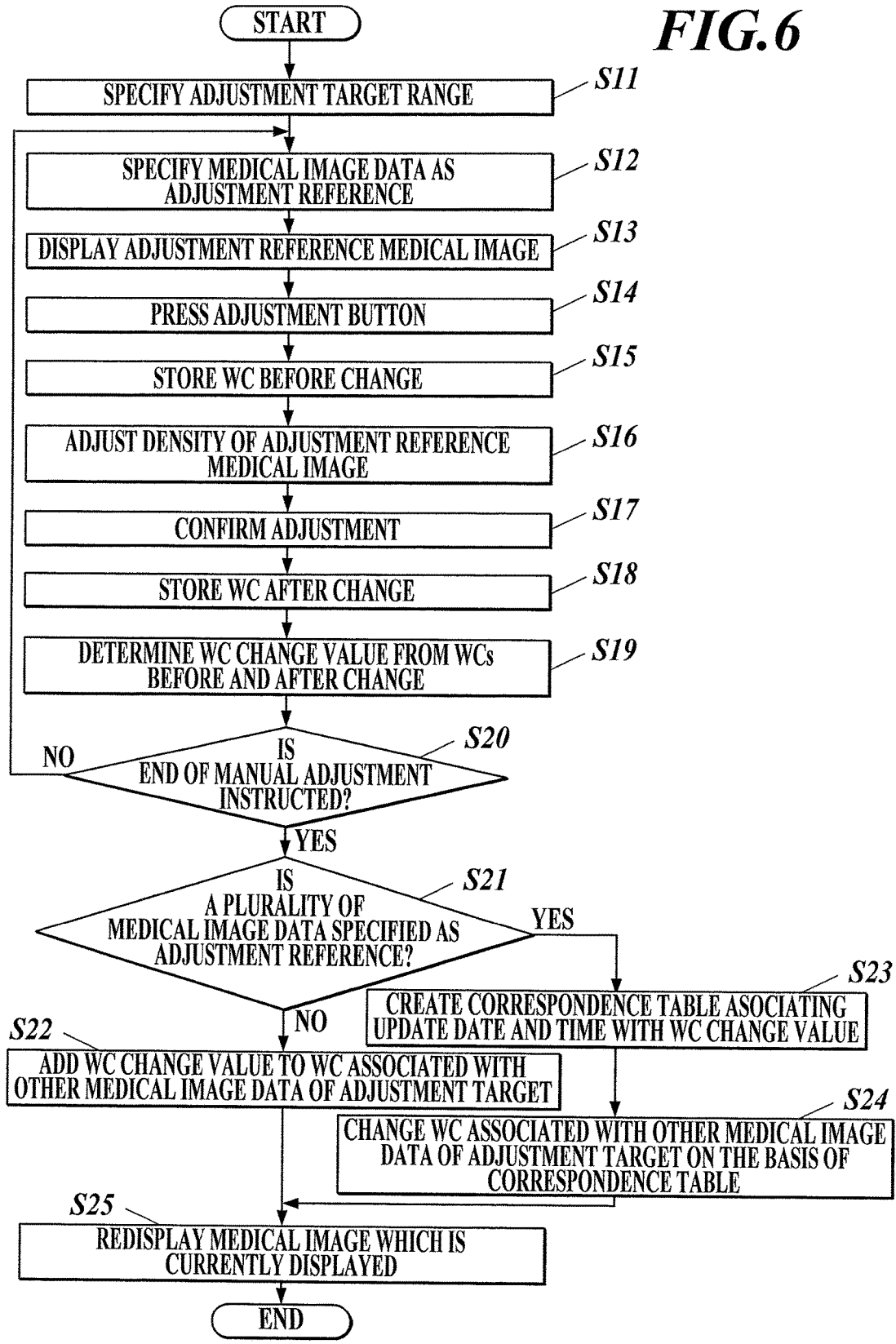
FIG. 6 is a flowchart showing density adjustment processing executed in the medical image display apparatus to which data was moved.

FIG. 6 is a flow chart showing density adjustment processing executed in the medical image display apparatus 30 after data movement. The processing is executed by software processing in cooperation between the control section 31 and the program stored in the storage section 35.

The user first specifies the adjustment target range for the plurality of pieces of medical image data stored in the storage section 35 by the operation to the operation section 32 (step S11). The adjustment target range can be specified by a predetermined classification of medical image data. The predetermined classification includes a modality type (CR, DX, CT and such like), an apparatus type, an image size (a half, a quarter and such like), a site (chest, hand and such like), a patient and combinations thereof. For example, the adjustment target range is specified to the modality type of "CR", image size of "half" and site of "chest".

On the basis of the information in the headers of the plurality of pieces of medical image data stored in the storage section 35, the control section 31 extracts medical image data included in the specified adjustment target range and controls the display section 33 to display a list of the medical image data included in the adjustment target range.

Next, when medical image data as the adjustment reference is specified from the list of medical image data included in the adjustment target range by user's operation to the operation section 32 (step S12), the control section 31 reads out the specified medical image data from the storage section 35, and controls the display section 33 to display an adjustment reference medical image on the basis of the read medical image data and the WC associated with the medical image data (step S13). Specifically, the control section 31 performs window level conversion processing to the medical image data by using the WC and WW contained in the header of the medical image data and outputs the gray level after conversion to the display section 33.

Figure 7:
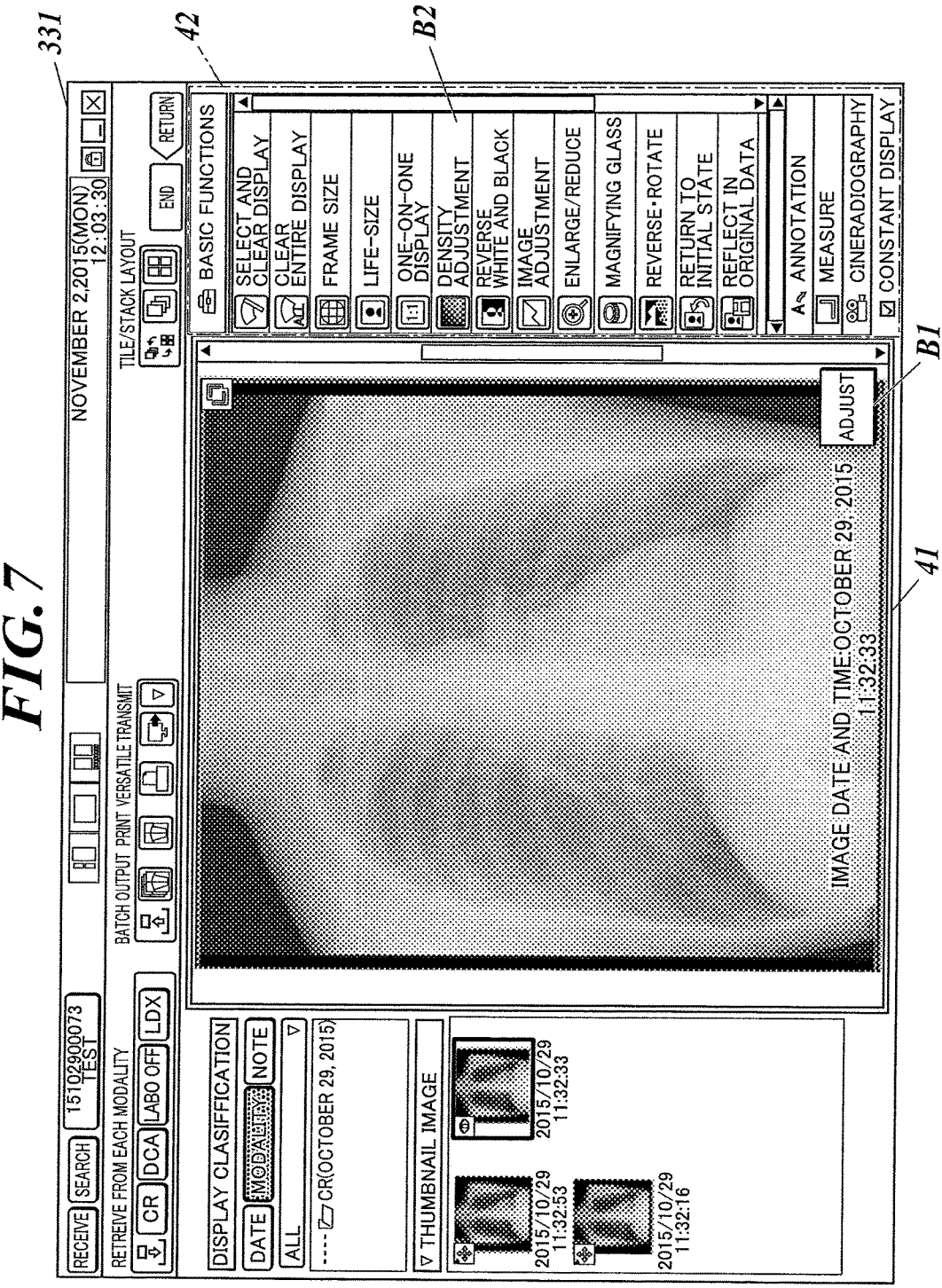
FIG. 7 is a screen example of an image display screen.

FIG. 7 shows a screen example of an image display screen 331 displayed on the display section 33. The image display screen 331 includes an image display region 41, a basic function specification region 42 and such like. The image display region 41 is a region for displaying the adjustment reference medical image. The basic function specification region 42 is a region for displaying buttons for specifying various basic functions performed to the medical image displayed in the image display region 41. An adjustment button B1 is also displayed in the image display region 41. The adjustment button B1 is pressed for starting adjustment to the medical image displayed in the image display region 41.

Next, when the user presses the adjustment button by the operation to the operation section 32 (step S14), the control section 31 acquires the WC (WC before change) associated with the medical image data from the header of medical image data as the adjustment reference, and stores the acquired WC before change in the storage section 35 (step S15).

Next, the control section 31 performs density adjustment of the adjustment reference medical image according to the user's operation to the operation section 32 (step S16).

Specifically, when the user presses, by the operation to the operation section 32, the density adjustment button B2 in the basic function specification region 42 of the image display screen 331 shown in FIG. 7, the image density can be changed by rotating the mouse wheel forward and backward. By the density adjustment of image, the WC associated with the adjustment reference medical image displayed in the image display region 41 is changed.

Figure 8:
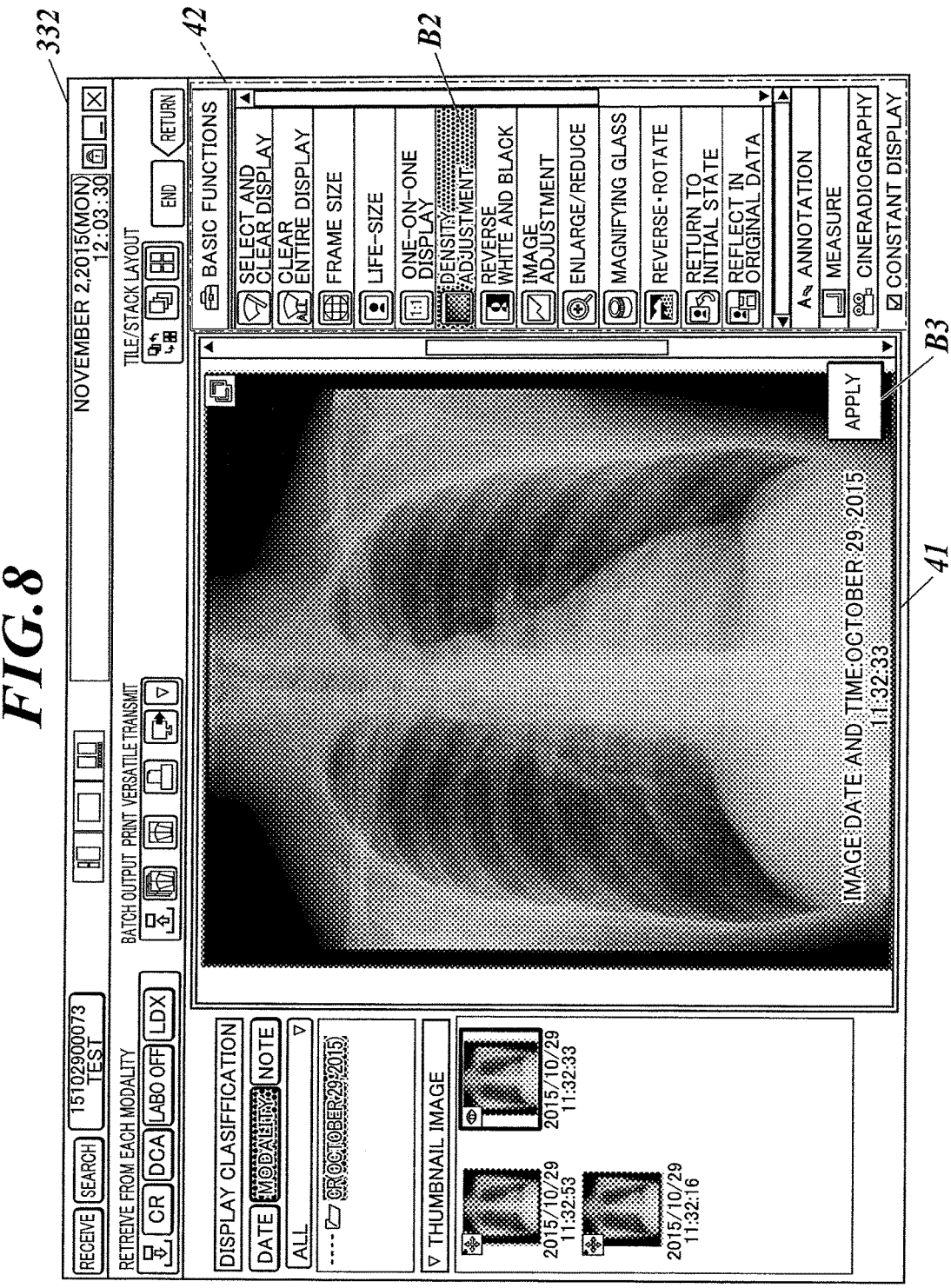
FIG. 8 is a screen example of an image display screen.

FIG. 8 shows an image display screen 332 after the density adjustment. In the image display screen 331 shown in FIG. 7, the medical image displayed in the image display region 41 is excessively bright and not appropriate for image interpretation. On the other hand, in the image display screen 332 shown in FIG. 8, the density of medical image in the image display region 41 is adjusted so that the medical image is displayed to be darker, and thus, the density is appropriate for image interpretation. In the image display region 41 of the image display screen 332, an application button B3 is displayed. The application button B3 is pressed when confirming the density adjustment performed to the image currently displayed in the image display region 41.

Next, when the user presses the application button B3 by the operation to the operation section 32, the control section 31 confirms the density adjustment which was performed to the adjustment reference medical image (step S17). The control section 31 stores the WC after change and the update date and time in the header of the medical image data as the adjustment reference to update the medical image data and stores the WC after change in the storage section 35 (step S18).

Next, the control section 31 determines the WC change value from the WCs before and after change (step S19). The WC change value is the value (difference) obtained by subtracting the WC before change from the WC after change. The control section 31 stores the update date and time and the WC change value of the medical image data as the adjustment reference in the storage section 35 so as to be associated with each other.

The control section 31 determines whether end of the manual adjustment is instructed by user's operation to the operation section 32 (step S20). If it is not determined that end of the manual adjustment is instructed (step S20: NO), the control section 31 returns to step S12 to repeat the processing.

In step S20, if it is determined that end of the manual adjustment is instructed (step S20: YES), the control section 31 determines whether a plurality of pieces of medical image data is specified as the adjustment reference (step S21).

If it is not determined that a plurality of pieces of medical image data is specified as the adjustment reference (step S21: NO), that is, if a single piece of medical image data is specified as the adjustment reference, the control section 31 adds the WC change value of the medical image data as the adjustment reference to a WC associated with medical image data (hereinafter, referred to as other medical image data of the adjustment target) which is other than the medical image data as the adjustment reference among the medical image data included in the adjustment target range. Specifically, for each piece of other medical image data of adjustment target, the control section 31 acquires the WC from the header of the other medical image data, stores a value obtained by adding the WC change value to the acquired WC as the WC after change in the header of the medical image data.

In step S21, if it is determined that a plurality of pieces of medical image data is specified as adjustment reference (step S21: YES), for each of the plurality of pieces of medical image data as the adjustment reference, the control section 31 creates a correspondence table associating the update date and time of the medical image data with the WC change value of the medical image data (step S23).

Next, the control section 31 changes the WC associated with the other medical image data of adjustment target on the basis of the correspondence table (step S24). Specifically, for each piece of the other medical image data of adjustment target, the control section 31 acquires the update date and time from the header of the medical image data, refers to the correspondence table and calculates the WC change value corresponding to the acquired update date and time by the interpolation method or the extrapolation method. For each piece of the other medical image data of adjustment target, the control section 31 acquires the WC from the header of the medical image data, adds the calculated WC change value to the acquired WC and stores the obtained value as the WC after change in the header of the medical image data.

After step S22 and step S24, the control section 31 redisplays the medical image currently displayed on the display section 33 by using the WC after change (step S25).

Then, the density adjustment processing is ended.

The above processing is repeatedly performed by changing the adjustment target range specified in step S11, and the density adjustment is finally performed to all the pieces of medical image data stored in the storage section 35.

In a case where the density adjustment processing can be executed on a uniform condition to all the pieces of medical image data stored in the storage section 35, all the pieces of medical image data stored in the storage section 35 may be specified as the adjustment target range.

When a medical image is displayed in the medical image display apparatus 30 after the above density adjustment processing, the control section 31 uses the WC after the adjustment which is associated with the medical image data. When the control section 31 displays a medical image on the display section 33 on the basis of the medical image data stored in the storage section 35, the control section 31 performs window level conversion processing to the medical image data by using the WC and WW contained in the header of the medical image data, and outputs the gray level after conversion to the display section 33.

As described above, according to the embodiment, since WCs associated with other medical image data are changed on the basis of the density adjustment result (change information) of the medical image data as adjustment reference in the medical image display apparatus 30, it is possible to easily perform density adjustment to have optimized densities without using special tools for medical image data subjected to density adjustment in another medical image display apparatus 10.

Specifically, it is possible to change each WC associated with the other medical image data of adjustment target on the basis of the WC change value indicating the difference between WCs before and after the adjustment, the WCs being associated with the medical image data as the adjustment reference.

In a case where a single piece of medical image data is the adjustment reference, the WC change value of the medical image data as the adjustment reference is added to the WC associated with each piece of medical image data other than the medical image data as the adjustment reference. Thus, adjustment similar to that of the medical image data as the adjustment reference can be performed to the other medical image data of adjustment target.

In a case where a plurality of pieces of medical image data is the adjustment reference, a correspondence table is created, the correspondence table associating update date and time of medical image data as the adjustment reference with the WC change value of the medical image data. Then, for each piece of medical image data other than the medical image data as the adjustment reference, the WC change value corresponding to the update date and time of the medical image data is calculated on the basis of the correspondence table, and the calculated WC change value is added to the WC associated with the medical image data. Thus, density adjustment can be performed according to the update date and time of medical image data.

For a plurality of pieces of medical image data, the density adjustment can be performed by specifying medical image data as the adjustment reference by the classification of modality type, apparatus type, image size, site, patient and such like.

The above description of embodiment is an example of medical image display apparatus according to the present invention, and the present invention is not limited to this. The detailed configurations and detailed operations of the sections forming the apparatus can also be modified appropriately within the scope of the present invention.

For example, the above embodiment has been described for a case of using WC as the density adjustment value. However, other values may be used as long as the value indicates the content of density adjustment which was performed to the medical image data.

The embodiment has been described for a case where the medical image data moved from the medical image display apparatus 10 to the medical image display apparatus 30 is a DICOM file generated in a format which meets the DICOM standard. However, the medical image data which is the density adjustment target may be RAW image. In a case of RAW image, information such as density adjustment value (WC or the like) and update date and time may be associated with the medical image data in another method without being contained in the header of the medical image data.

The above embodiment has been described by taking, as an example, a case of using a hard disk or a non-volatile semiconductor memory as the computer readable medium storing the programs for executing each processing. However, the present invention is not limited to this example. As other computer readable mediums, portable recording mediums such as a CD-ROM can be used. Further, as the medium for providing program data via a communication line, a carrier wave can also be used.

The entire disclosure of Japanese Patent Application No. 2016-011194 filed on Jan. 25, 2016 including description, claims, drawings, and abstract are incorporated herein by reference in its entirety.

What is claimed is:

1. A medical image display apparatus, comprising:
   a storage which stores a plurality of pieces of medical image data, each of the plurality of pieces of medical image data being moved from another medical image display apparatus and associated with a density adjustment value regarding a density which is adjusted when a medical image is displayed based on the medical image data in the another medical image display apparatus;
   a display which displays a medical image based on medical image data stored in the storage;
   an input device which receives a user's specification of medical image data as an adjustment reference among the plurality of pieces of medical image data stored in the storage; and
   a hardware processor configured to:
   control the display to display an adjustment reference medical image based on the medical image data as the adjustment reference and a density adjustment value associated with the medical image data as the adjustment reference;

receive a user's instruction to perform density adjustment of the adjustment reference medical image displayed on the display; and for each piece of medical image data other than the medical image data as the adjustment reference, from among the plurality of pieces of medical image data stored in the storage, change a density adjustment value associated with the medical image data based on change information indicating a content changed by the density adjustment performed to the adjustment reference medical image, wherein the change information is a change value indicating a difference between density adjustment values before and after the density adjustment, the density adjustment values being associated with the medical image data as the adjustment reference, wherein the medical image data as the adjustment reference comprises a plurality of pieces of medical image data, and wherein the hardware processor is further configured to:
for each of the plurality of pieces of medical image data as the adjustment reference, create a correspondence table associating an update date and time with the change value of the medical image data, the update date and time being a latest date and time when the density adjustment value associated with the medical image data is updated in the another medical image display apparatus; and for each piece of the medical image data other than the medical image data as the adjustment reference, calculate a change value corresponding to the update date and time of the medical image data based on the correspondence table and add the calculated change value to the density adjustment value associated with the medical image data.

2. The medical image display apparatus according to claim 1, wherein the input device is capable of receiving specification of the medical image data as the adjustment reference by a predetermined classification of the plurality of pieces of medical image data stored in the storage, and wherein the hardware processor is further configured to, for each piece of the medical image data other than the medical image data as the adjustment reference, from among the plurality of pieces of medical image data stored in the storage, change the density adjustment value associated with the medical image data based on the change information which is obtained by the predetermined classification.

3. The medical image display apparatus according to claim 2, wherein the predetermined classification is a modality type, an apparatus type, an image size, a site, a patient or a combination thereof.

4. A medical image adjustment method for a medical image display apparatus that includes: a storage which stores a plurality of pieces of medical image data, each of the plurality of pieces of medical image data being moved from another medical image display apparatus and associated with a density adjustment value regarding a density which is adjusted when a medical image is displayed based on the medical image data in the another medical image display apparatus; and a display which displays a medical image based on medical image data stored in the storage, the method comprising:

receiving a user's specification of medical image data as an adjustment reference among the plurality of pieces of medical image data stored in the storage;

controlling the display to display an adjustment reference medical image based on the medical image data as the adjustment reference and a density adjustment value associated with the medical image data as the adjustment reference;

receiving a user's instruction to perform density adjustment of the adjustment reference medical image displayed on the display; and for each piece of medical image data other than the medical image data as the adjustment reference, from among the plurality of pieces of medical image data stored in the storage, changing a density adjustment value associated with the medical image data based on change information indicating a content changed by the density adjustment performed to the adjustment reference medical image, wherein the change information is a change value indicating a difference between density adjustment values before and after the density adjustment, the density adjustment values being associated with the medical image data as the adjustment reference, wherein the medical image data as the adjustment reference comprises a plurality of pieces of medical image data, and wherein the method further comprises:
for each of the plurality of pieces of medical image data as the adjustment reference, creating a correspondence table associating an update date and time with the change value of the medical image data, the update date and time being a latest date and time when the density adjustment value associated with the medical image data is updated in the another medical image display apparatus; and for each piece of the medical image data other than the medical image data as the adjustment reference, calculating a change value corresponding to the update date and time of the medical image data based on the correspondence table and adding the calculated change value to the density adjustment value associated with the medical image data.

5. A non-transitory computer readable recording medium storing a program for a computer of a medical image display apparatus that includes: a storage which stores a plurality of pieces of medical image data, each of the plurality of pieces of medical image data being moved from another medical image display apparatus and associated with a density adjustment value regarding a density which is adjusted when a medical image is displayed based on the medical image data in the another medical image display apparatus; and a display which displays a medical image based on medical image data stored in the storage, the program causing the computer to execute processing comprising:

receiving a user's specification of medical image data as an adjustment reference among the plurality of pieces of medical image data stored in the storage;

controlling the display to display an adjustment reference medical image based on the medical image data as the adjustment reference and a density adjustment value associated with the medical image data as the adjustment reference;

receiving a user's instruction to perform density adjustment of the adjustment reference medical image displayed on the display; and for each piece of medical image data other than the medical image data as the adjustment reference, from among the plurality of pieces of medical image data stored in the storage, changing a density adjustment value associated with the medical image data based on change information indicating a content changed by the density adjustment performed to the adjustment reference medical image, wherein the change information is a change value indicating a difference between density adjustment values before and after the density adjustment, the density adjustment values being associated with the medical image data as the adjustment reference, wherein the medical image data as the adjustment reference comprises a plurality of pieces of medical image data, and wherein the program causes the computer to execute further processing comprising:

for each of the plurality of pieces of medical image data as the adjustment reference, creating a correspondence table associating an update date and time with the change value of the medical image data, the update date and time being a latest date and time when the density adjustment value associated with the medical image data is updated in the another medical image display apparatus; and for each piece of the medical image data other than the medical image data as the adjustment reference, calculating a change value corresponding to the update date and time of the medical image data based on the correspondence table and adding the calculated change value to the density adjustment value associated with the medical image data.

* * * * *